United States Patent [19]

Warren et al.

[11] 4,282,487
[45] Aug. 4, 1981

[54] SUBSEA HYDROCARBON SENSOR SYSTEM

[75] Inventors: Walter B. Warren, Seabrook; Ronald J. Marosko, Houston, both of Tex.

[73] Assignee: TRW Inc., Redondo Beach, Calif.

[21] Appl. No.: 78,944

[22] Filed: Sep. 26, 1979

[51] Int. Cl.$^3$ .............................................. G01N 27/02
[52] U.S. Cl. .................................... 324/445; 324/204
[58] Field of Search ............... 324/445, 204, 220, 221; 204/219, 221

[56]  References Cited

U.S. PATENT DOCUMENTS

| | | | |
|---|---|---|---|
| 2,832,046 | 4/1958 | Rezek | 324/445 |
| 2,985,822 | 5/1961 | Georgi | 324/221 |
| 3,054,946 | 9/1962 | Esterson | 324/445 |
| 3,292,077 | 12/1966 | Sloughter | 324/445 |
| 3,389,332 | 6/1968 | Ketcham | 324/445 |
| 3,491,287 | 1/1970 | Brown | 324/445 |
| 3,510,761 | 5/1971 | Brown | 324/445 |
| 3,603,873 | 9/1971 | Cirulis | 324/445 |
| 3,855,522 | 12/1974 | Kobayashi | 324/445 |
| 3,867,688 | 2/1975 | Koski | 324/445 |
| 3,987,362 | 10/1976 | McCann et al. | 324/445 |

Primary Examiner—Stanley T. Krawczewicz
Attorney, Agent, or Firm—Ben DeWitt; John J. Connors

[57] ABSTRACT

A hydrocarbon detection system is provided for use in a subsea hydrocarbon production installation which includes production tree assemblies, an electrohydraulic control module located on the sea floor and remote from the production trees, cable assemblies interconnecting the control module with the production trees through magnetic coupling devices. A pair of inductive elements are electrically coupled by the surrounding sea water. Displacement of the conductive sea water by escaping hydrocarbons affects the coupling between the inductive elements to produce a hydrocarbon-presence-responsive output signal. The inductive elements are resonated within a selected frequency range by capacitors coupled with a primary inductor coil by auxiliary windings on a common core element. An excitation signal sweeps over the selected frequency range at a rate effective to produce a peak detected signal at the resonant frequency. The peak output signal is then monitored to form a control signal functionally related to the presence or absence of hydrocarbons in the sea water.

17 Claims, 6 Drawing Figures

SUBSEA HYDROCARBON SENSOR SYSTEM

BACKGROUND OF THE INVENTION

This invention relates to systems for ascertaining the presence of hydrocarbons in an environmental medium and, more particularly, to improved methods and apparatus using inductive coupling to generate and sense induced current in a conductive environmental medium and thereby detect changes in the conductivity of such medium.

It is well known that hydrocarbons, such as crude oil and natural gas, are being produced in increasing quantities worldwide to supply growing energy needs. However, the uncontrolled release of hydrocarbons into the environment can produce substantial environmental degradation. Accordingly, the production of hydrocarbons is generally done in a controlled system.

One particular environment where increasing quantities of hydrocarbons are being produced is the subsea floor at various offshore locations. This production is being obtained at ever-increasing depths which are generally hostile or inaccessible to production personnel. Accordingly, there is usually provided a surface platform for monitoring and controlling the production at the subsea location and various elements are located on the ocean floor responding to the surface controls. An entire production unit may consist of a central production platform, a subsea gathering station, several central control platforms having wells associated with them and further controlling satellite wells about the control module.

All of the above units must be interconnected by production piping having joints suitable for use in the hostile seawater environment and from which hydrocarbons might escape from the production system. It is also apparent that prompt detection of incipient hydrocarbon leaks is a difficult task in the submerged environment.

Desirably, a plurality of detection units would be provided placed at locations with a likelihood of hydrocarbon escape. Such locations, for example, would be adjacent the control unit attachment to the well casing, adjacent pipe joints, adjacent underwater storage tanks, or around various valving for controlling the flow of hydrocarbons. Desirably, the presence of hydrocarbons in small quantities should produce an output indication which can be transmitted to a surface location to alert production personnel that corrective action is needed.

The high conductivity of sea water has been utilized in prior devices for measuring the salinity of seawater. If a toroidal inductive element is immersed in the sea and electrically excited, a magnetic field is generated within the toroid which produces an electrical current in the adjacent seawater. A second toroidal inductive element may be used to detect the resulting circulating electrical current to produce an output signal which is related to the circulating current in the environmental medium.

Various prior patents teach the use of coupled toroidal inductors to measure water salinity. For example, in U.S. Pat. No. 3,292,077 to Sloughter, the output from the detecting inductive element controls a voltage controlled oscillator and thereby produces a signal of a frequency functionally related to the conductivity of the seawater. In U.S. Pat. No. 3,855,522 to Kobayashi, U.S. Pat. No. 3,510,761 to Brown, and U.S. Pat. No. 3,603,873 to Cirulis, various secondary windings are provided on the torodial elements to obtain improved features such as automatic zeroing, reference signals, and temperature compensating signals. Other U.S. Pat. No. 3,491,287 to Brown and U.S. Pat. No. 3,389,332 to Ketcham, illustrate various improvements in systems using inductive elements for precision measurements of salinity.

The detection of hydrocarbons escaping from a subsea production system does not require a precision measurement of seawater salinity; but does require a system which produces a highly reliable output indication functionally related to the presence or absence of hydrocarbons. This output signal must also be obtained while the system is packaged in the manner necessary for long term reliable operation exposed to the pressure and temperatures associated with a subsea environment and the corrosive effects of the sea water. It is believed that one prior device uses the inductive coupling technique discussed above for salinity measuring apparatus, positioned in an inverted bucket-type housing to determine the presence of hydrocarbons. Escaping hydrocarbons are captured within the housing, displacing the sea water from the housing, changing the conductivity of the environmental medium surrounding the coupled inductive elements, and producing a corresponding change in the voltage induced in the second toroidal inductor. Once a predetermined change in the induced voltage occurs, an alarm is triggered to initiate corrective action.

There are, however, problems with operating the prior art devices in a subsea production system. Frequently the sensors are located at some distance from the central production platform or subsea control module and this necessitates interconnecting signal cables. A particularly suitable connecting cable interconnects with extending portions of cable by using magnetic coupling elements. In this manner, the mechanical difficulties associated with sealing about a plurality of extending conductor elements are avoided. However, significant signal attenuation and/or distortion can occur through these connecting elements. To maintain adequate signal strength for high-reliability hydrocarbon detection it has been necessary to provide for signal amplification and conditioning within the subsea signaling system. But the addition of such active circuits tends, per se, to lessen the overall system reliability. For this as well as other reasons, it is desirable to minimize the number of active components which must be placed in the ocean environment.

Further, it will be appreciated that the signal should remain sufficiently strong to accommodate variations in the attenuation through the cable connectors as a result of varying sea water temperature and pressures and through possible corrosion and fouling associated with the underwater environment. Spurious indications can significantly disrupt production, resulting in extremely expensive and time consuming shutdowns for underwater inspection. Thus, a sensitive and highly reliable sensor system must be provided.

It is desirable to form the toroidal elements with a minimum number of turns in order to maximize the amplitude of the signal across the receiving inductor load. Where both a transmitting and a receiving toroidal element are provided with the same number of turns, N, it can be shown that:

$$V_{out} = V_{excitation} [1/(1+N^2 R_m/R_s)]$$

where

- $V_{out}$ = voltage across receiver load
- $V_{excitation}$ = voltage across transmitter turns
- $N$ = number of coil turns on each of transmitter and receiver elements
- $R_s$ = equivalent resistance of surrounding environmental medium
- $R_m$ = equivalent resistance of receiver load Thus, the excitation signal is attenuated in inverse proportion to the square of the number of coil turns.

Reducing the number of coil turns, however, reduces the inductive reactance of the transmitter inductive element. A reduced reactance acts to reduce $V_{exciting}$ since the actual input signal voltage is determined by the ratio of the coil reactance to the total reactance of the transmitter cable and coil.

Also, the magnetic characteristics of the materials forming inductive sensing elements change as a function of temperature. It has been found that the temperature changes are less pronounced for core elements having a low magnetic permeability. Thus, to avoid temperature-dependent signal fluctuations it would be desirable to use these low permeability materials. However, the low permeability core materials further reduce the inductive reactance of the toroidal inductors, which reduces the signal throughput between the transmitter and receiver elements.

As hereinafter discussed, one aspect of the present invention relates to increasing detection sensitivity by providing a resonant circuit in either the transmitting or detecting inductive elements, or both. This requires capacitive elements which are capable of withstanding the hostile environment at the subsea locations. However, relatively low frequencies are used in the underwater signal system to reduce signal attenuation, normally necessitating large values of capacitance to resonate the torodial inductor at appropriate frequencies. Large capacitors having the requisite stability, lifetime, and resistance to subsea pressure and temperature conditions are difficult to obtain and inordinately expensive. Typically, available large capacitors are rolled foil-type capacitors with varying internal void spaces. Subsea pressures act to collapse these voids unless one-atmosphere pressure enclosures are provided. In contrast, smaller capacitors are formed of solid plate-type elements capable of withstanding the pressure.

It will also be appreciated that the hydrocarbon sensor system must be capable of accommodating a variety of temperature and pressure conditions which affect the magnetic characteristics of the toroidal core element and, hence, the inductance of the inductive element. Thus, the resonant frequency of an LC circuit, if provided, will not be a constant value but will vary about some predetermined design value.

These problems are also overcome by the present invention, however, and improved methods and apparatus are provided for reliably monitoring the subsea environment for the presence of escaping hydrocarbons.

SUMMARY OF THE INVENTION

An improved hydrocarbon sensor system is provided which monitors the conductivity of the environmental medium surrounding the sensor assembly to detect the presence or absence of hydrocarbons and to generate an output signal indicating the presence of hydrocarbons in the sea water. In a preferred embodiment, a pair of toroidal inductive elements are spaced-apart so that the transmitting inductive element produces a circulating current in the surrounding conductive medium, and the circulating current is detected by the receiving inductive element, the magnetic field associated with the circulating current inducing a voltage output from the second inductive element. Under normal conditions, wherein the inductive elements are surrounded by substantially homogenous sea water, the A-C signal generated by the receiving inductive element will be of substantially constant amplitude. The signal is subject to attenuation to a degree dependent upon the length and signal transmissivity of the cables and coupling elements that may be required between the hydrocarbon sensor system and a centrally located subsea control module.

In the present system, the receiving inductive element, the transmitting inductive element, or both, may cooperate with associated capacitive elements to form a resonant circuit which increases the system sensitivity for signal detection. In a particular embodiment, capacitance for tuning one or both inductive elements to resonance is provided by appropriate capacitive elements connected to one or more auxiliary windings on the inductive element core. These capacitive elements are then reflected into the primary of the inductive element through transformer action. The reflected capacitance may be a larger value as required to obtain a desired resonant frequency, where a suitable ratio of the number of auxiliary winding turns to number of primary turns is provided. The reflected capacitance is proportional to the square of the turns ratio, permitting a small capacitive value to be used in the sensor assembly, where capacitive elements having small capacitance values are more ruggedly constructed and easier to obtain for use in the subsea environment.

In accordance with another aspect of the invention, a frequency sweeping signal is used for exciting the inductive elements. This compensates for changing resonant conditions as a function of environmental parameters, e.g. temperature. The frequency range over which the signal is modulated is selected to cover the expected range over which the resonant frequency of the indicative element may drift and to obtain a peak output within the sweeping range. A peak detection system may be included in the receiver system to provide an output indication functionally related to the peak signals received from the system. The system thus constructed acts to provide well defined output signals which may be reliably detected over a wide range of operating conditions to yield an output signal related to the presence of hydrocarbons in the associated subsea hydrocarbon production system.

It is a feature of the present invention to provide a reliable hydrocarbon sensor system suitable for use in a subsea environment.

It is another feature of the present invention to provide an inductively coupled hydrocarbon sensor system using resonance to increase system sensitivity.

Yet another feature of the present hydrocarbon detection system is to provide a reliable signal output over a wide range of system operating temperatures.

It is a feature of the present invention to use a signal which is frequency modulated over a range that includes the resonant frequency of the inductive elements.

It is a feature of the present invention to employ only small capacitive values in obtaining the desired resonant frequency.

Thus, it is a feature of the present invention to provide a hydrocarbon sensor system comprising a transmitting inductive element responsive to an excitation signal for generating an electrical current in an environmental medium adjacent the transmitting element, a receiving inductive element responsive to the electrical current in the surrounding medium for providing an output signal, wherein at least one of the inductive elements has an associated capacitive element to form a circuit resonant within a predetermined frequency range, with a frequency sweeping generator producing the exciting signal covering at least the predetermined frequency range so that a reliably distinctive signal output is obtained.

Another feature of the present invention is to provide a tuned inductive element having a primary coil wound about a core a first number of turns, an auxiliary coil wound about the core a second number of turns with a capacitor connected across the auxiliary coil, where the ratio of the first number of turns to the second number of turns is effective to reflect a capacitance from the capacitor to resonate with the primary coil within a predetermined frequency range.

One other feature of the present invention is to provide an improved method for detecting the presence of hydrocarbons in a conductive medium by generating a frequency sweeping signal over a selected frequency range, applying the frequency sweeping signal to a first inductive element to induce an electrical current in the surrounding conductive medium, detecting the induced electrical current with a second inductive element to obtain an output signal, where at least one of the inductive elements is tuned to resonance at a frequency within the selected frequency range, and monitoring the resultant output signal which is related to the presence of hydrocarbons.

These and other features and advantages of the present invention will become apparent from the following detailed description, wherein reference is made to the figures in the accompanying drawings.

IN THE DRAWINGS

Figure 1:
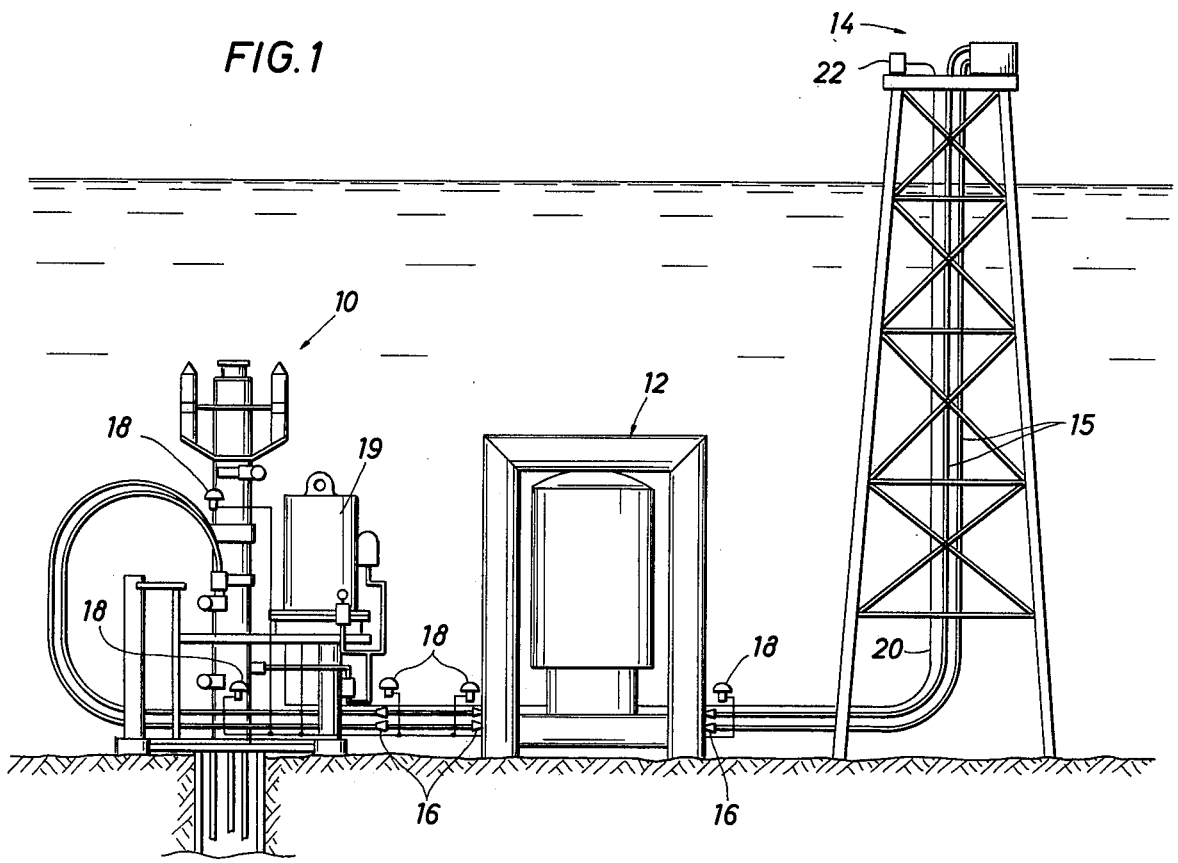
FIG. 1 is a pictorial illustration of a subsea production installation embodying the invention.

Referring now to FIG. 1, there is illustrated various components of a subsea production system. A subsea production tree 10 is provided over a borehole and generally acts to control the flow of hydrocarbons from the earth formations. Production tree 10 may contain various electronic control assemblies and hydraulically-actuated control valves to provide both normal and emergency control of the hydrocarbon production. In some instances, an intermediate station 12 may be provided to collect the produced hydrocarbons and/or provide a central control location for a plurality of satellite wells spaced as much as several miles from the intermediate station.

A third installation component may be a platform 14 having a portion above the surface of the sea for occupancy by production personnel and for monitoring and controlling the various production facilities. Platform 14 may contain various equipment for monitoring and controlling the subsea operations and may also serve as a surface exit for various pipes 15, power cables and control signal conductors. Pipes 15 generally run from the platform 14 to intermediate station 12 or directly to a production tree 10. Thus, several subsea pipe connections may be required in forming the interconnected production system.

Hydrocarbon leakage may occur at various locations in the production system. One location for leakage is adjacent the various well boreholes beneath the production trees 10. Hydrocarbon leakage may also occur at various pipe interconnection locations and at other locations in the system, depending upon the specific system design. As hereinabove discussed, it is desirable to detect the presence of leaking hydrocarbons at an early stage to initiate prompt remedial action. Thus, sensor elements 18 may be placed throughout the system at locations where hydrocarbon leakage is likely to occur. Sensors 18 may be mounted at various locations about the production tree 10, at locations adjacent pipe connection 16, or at other locations considered desirable. Because of the subsea location these sensor assemblies 18 are not readily replaceable and need to be highly reliable when operating in the subsea environment.

If the sensor assemblies are permanently mounted and designed in a manner which can withstand the high pressure and corrosive subsea environment, it is desirable to provide the electronic components associated with the sensor at a remote location where replacement is possible. In some arrangements, this is done by placing the electronics in a hermetically sealed subsea control package 19 which may be located on production tree 10 and readily removable and replaceable thereon. In another arrangement, the electronics may be provided on production platform 14 for ready access. Since the sensor element and the electronics package 19 preferably are arranged for separate retrieval to the surface, the system preferably includes various cable connections associated with a subsea installation, as hereinafter described.

Generally, sensor elements 18 sense the conductivity of the surrounding medium to determine the presence of hydrocarbons. As hereinafter discussed, a sensor assembly may be inserted in an inverted-type bucket where escaping hydrocarbons will collect and displace sea water until a sufficient change in conductivity is obtained to trigger a suitable indicator. Thus, so long as sea water is present a normal output signal is obtained. When the very low conductivity hydrocarbons displace the sea water, the output signal is substantially diminished, or entirely lost, providing a reliable positive indication of the presence of hydrocarbons.

Figure 2:
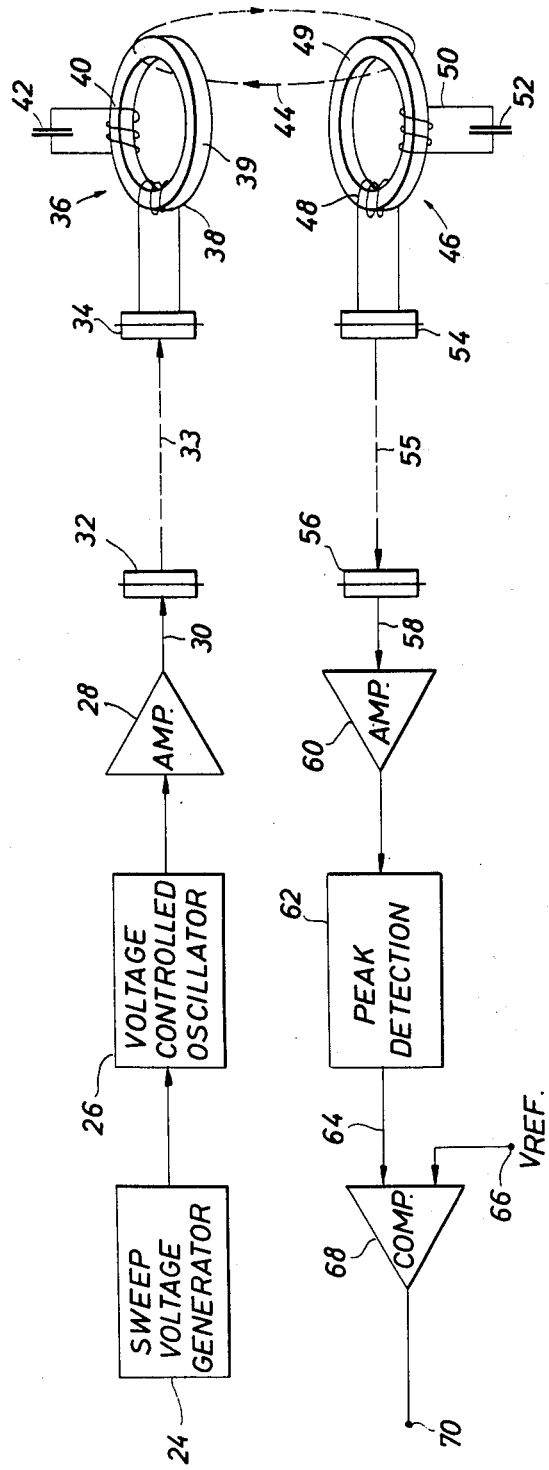
FIG. 2 is a block diagram of one embodiment of apparatus in accordance with the invention.

Referring now to FIG. 2, there is depicted a block diagram showing a hydrocarbon detection system in accordance with the invention. The sensing system comprises two inductive elements 36 and 46 generally placed in a side-by-side relationship. Inductive element 36 preferably is formed using a closed core element 39 and, since it is desired to confine the mangentic flux to the core element 39, a toroidal shaped core element is preferable. A primary winding 38 is provided for inducing an alternating magnetic flux in core 39. Inductive element 46 preferably is identical to inductive element 36, having a toroidal core element 49, and a winding 48 for producing an output signal.

As hereinafter discussed, inductive element 36 will be referred to as the transmitting inductive element where an exciting signal is applied to winding 38 to generate an alternating magnetic flux within core 39. Inductive element 46 will be referred to as the receiving inductive element. The magnetic field of core 39 induces an alternating current passing along line 44 through the interior of core 49 and linking the two cores. The induced alternating flux in core 49 produces an induced voltage in winding 48 to produce the desired output signal. Assuming that a conductive medium is adjacent the interior of the inductive elements 36 and 46, and in the volume about inductive elements 36 and 46 to form at least one closed conducting loop, the operation of the system is similar to a one turn transformer.

Receiving inductive element 46 is placed at a location adjacent inductive element 36 whereby circulating current 44 passes through toroidal core 49. Desirably, the spatial relationship between inductive elements 36 and 46 is such that the current passing through inductive element 46 is maximized. The two cores are placed in a subsea region that is normally occupied by sea water and in which it is desired to promptly detect the presence of oil or gas.

Still referring to FIG. 2 and to inductive elements 36 and 46, there may be seen capacitive elements 42 and 52 associated therewith, respectively. As hereinabove described, inductive elements 36 and 46 are located remotely from the active electronic components hereinafter described. The excitation signal must pass through a plurality of magnetic couplers 32, 34 along cable 33 before arriving at the element 36, resulting in an attenuated signal. Similarly, the output signal from winding 48 must pass through magnetic couplers 54, 56 and through interconnecting cable 55 to reach the signal processing circuitry 60, 62 and 68.

The sensitivity of the system is further reduced if low permeability core materials are used in an effort to reduce the variations in signal output as a function of temperature. The low magnetic permeability of the material results in a lower inductive reactance at the transmitting coil 38. Thus, a given signal produces a reduced excitation voltage across the coil, resulting in a reduced output signal along path 44.

It has been found that the sensitivity of the system can be greatly increased by providing resonating capacitors with the inductive elements. As hereinabove explained, it is desirable to maximize the effective reactance of the transmitter coil 38 and the receiver coil 46. The resonant circuit greatly increases the effective reactance of transmitting element 36 to maximize the signal voltage appearing across coil 38. Likewise, a resonant circuit acts to increase the effective reactance of the receiving circuit 46 relative to the circulating current path 44 to increase the relative signal transmitted to the receiver 46 and appearing across coil 48.

The resonant circuit may be formed in either transmitting inductive element 36, receiving inductive element 46, or in both elements. This resonant circuit provides a greatly enhanced signal at the resonant frequency. This resonant frequency is inversely proportional to the square root of the product of the inductance and the capacitance. Since only low inductances are provided by coils 38 and 48, and since desirable operating frequencies are only in the kilohertz range to reduce operating power losses, large values of capacitance would be required if the windings 38 and 48 were to be resonated by direct connection of capacitors across these windings.

Ordinarily, a resonant circuit would be formed by connecting a capacitor in parallel with the inductive element. In the system herein described, this arrangement would require a capacitor connected across the primary coils 38 and 48 of the inductive elements. However, this arrangement requires large capacitance values to resonate at the desired frequency. Although large capacitors can be obtained, it is difficult and undesirably expensive to obtain such large capacitors with the necessary temperature stability, reliabilty, and ambient pressure tolerance required for subsea use.

In accordance with the invention, this difficulty is avoided by using the transformer properties of the toroids and providing an auxiliary winding with the capacitive element connected across the auxiliary winding. As shown for inductive element 36, an auxiliary winding 40 is provided on toroidal core 39, and a relatively small capacitance element 42 is connected across the end leads of winding 40. The value of capacitance 42 is reflected back to the primary winding, as hereinafter discussed. Referring to inductive element 36 in FIG. 2, assume that capacitor 42 is represented by $C_2$ and secondary winding 40 has $N_2$ number of turns. If the number of turns in the primary winding is $N_1$, then the capacitance reflected to the primary may be represented as $C_1 = C_2 (N_2/N_1)^2$. Thus, the capacitance required to resonate primary coil 38 is reduced by the square of the turns ratio. For example, a suitable inductive element was constructed where $N_1$ was ten turns and $N_2$ was fifty turns, permitting a reduction in the value of capacitor required for resonance by 25:1. Capacitors having this twenty-five times smaller capacitance value are more readily obtained, more ruggedly constructed, better suited for the compact packaging desired for the sensor assembly, and are far better able to tolerate the high ambient pressure of the subsea environment.

Using the design hereinabove discussed, a compact sensor assembly may be constructed using resonant circuits for the transmitting inductive element 36, receiving inductive element 46, or both, to greatly enhance the sensitivity of the sensor system. This enhanced sensitivity can be effectively utilized, however, only so long as the excitation signal corresponds in frequency with the resonant frequency of the tuned indicative element. It will be appreciated that a constructed sensor assembly must operate at varying conditions of pressure and temperature, which act to vary the resonant frequency of the system over some range of frequencies. A particularly pronounced effect is produced by the temperature variance of the permeability of the magnetic material comprising the core elements 39, 49 even where low permeability materials are used. In accordance with the invention, this difficulty is resolved by the use of a frequency modulated excitation signal source in combination with the hydrocarbon-detecting inductive elements.

Referring again to FIG. 2, there are depicted various elements of a signal generating system and a signal detecting system, in block diagram form, according to a preferred embodiment of the present invention. In order to overcome the problem associated with a shifting resonant frequency of the inductive elements, hereinabove discussed, a variable frequency exciting signal is employed. In a preferred embodiment, the frequency of the exciting signal is regularly varied over a predetermined frequency range which is selected to accommodate the expected variation in resonant frequencies of the inductive elements 36 and 46. Such an excitation signal preferably is generated by combining a sweep voltage generator 24 with a voltage controlled oscillator 26. Sweep voltage generator 24 may produce a sawtooth-waveform voltage which varies as a function of time and preferably repeats at a frequency of about 40 Hz. The sweep rate is low enough to permit a peak output to be obtained at the resonant condition and high enough to use a peak detector as hereinbelow discussed. This output voltage is applied to control the frequency of voltage controlled oscillator 26 so that is generates an output frequency which varies in response to the sweep voltage generator 24 output. Thus, a frequency modulated (FM) signal is generated and applied to amplifier 28 for the power amplification necessary to drive transmitting inductive element 36. In one embodiment, the frequency of the excitation signal is swept from 75 to 100 KHz with the sweep across this range being repeated about 40 times per second.

As briefly discussed above, the output signal 30 from amplifier 28 is produced within a hermetically sealed electronic control module at a location remote from the sensor elements and is transmitted to the sensor element by interconnecting cable 33 which may include a plurality of connector elements 32 and 34. For subsea applications, connector elements 32 and 34 preferably are magnetic-type signal couplers to eliminate the need for sealing about extending pin-type connectors. A conventional single-phase power and signal coupler is described in Paper No. 3357 presented at the 11th Annual Offshore Technology Conference, Apr. 30 through May 3, 1979, "A High Integrity Electronic Subsea Production Control System", by Locheed et al.

However, significant signal attenuation occurs in passing signals through the magnetic coupling elements to the transmitting inductive element 36. The two inductive elements, one or both of which may be resonant, substantially assist in maximizing signal transfer at the sensor element.

If transmitting inductive element 36 includes a resonating capacitor 42, then a peak signal output will occur as FM signal 30 passes through the resonant frequency. Thus, a peak output will be obtained from receiving inductive element 46 at that frequency. If receiving inductive element 46 is tuned to the same resonant frequency as inductive element 36, or within a selected bandwidth thereof, the resonant effect will be reinforced and the output signal will have a more pronounced peak output. In any event, a tuned receiving inductive element 46 will obtain a peak output as FM signal 30 passes through the resonant frequency obtained from inductive element 36 and inductive element 46.

The resulting output signal from receiving inductive element 46 appears across primary coils 48 for transmission back along the signal cable to signal detection circuitry. This output signal passes through one or more magnetic signal couplers 54, through interconnecting cable 55, through one or more signal couplers 56 to the output circuitry. Thus, signal 58 is further attenuated and is first presented to amplifier 60 before processing. Signal 58 is an FM signal having an amplitude modulation as a result of the various resonant sensor elements, with the peak amplitude being functionally related to the conductivity of the environmental medium surrounding sensor elements 36 and 46.

Referring still to FIG. 2, there is shown one embodiment for obtaining the desired output signal 70 indicating the presence of hydrocarbons in the environmental medium surrounding the sensor elements. Signal 58 is amplified and presented to a peak detection circuit 62 which operates to provide an output signal, functionally related to the peak amplitude of the amplitude modulated FM signal 58, to a comparator 68. Thus, peak detection circuit 62 response is such that the output corresponds to the peak amplitude value of incoming FM signal 58. This enables the production of a detected signal 64 whose amplitude depends primarily on the presence or absence of hydrocarbons (e.g., oil or gas) in the vicinity of elements 36 and 46, and not upon the temperature-dependent frequency at which these elements may be resonant at a particular time.

Peak signal 64 may be presented to comparator 68 which then compares signal 64 with a preselected reference voltage 66, selected to represent a signal level indicating the presence of hydrocarbons. When signal voltage 64 drops below reference voltage 66, comparator 68 generates output signal 70 to indicate that environmental conductivity has decreased below a selected value, thereby indicating the presence of hydrocarbons at the sensor. Output signal 70 may be used in any variety of ways to alert further control circuitry or personnel to the environmental condition.

Peak signal 64 may also be used directly as an analog indication of the relative amount of hydrocarbons about sensor elements 34, 46. If desired, signal 64 would then be transmitted for processing and display to operating personnel.

Thus, the system hereinabove described and depicted in FIG. 2 constitutes a sensitive system capable of reliably detecting the presence of hydrocarbons adjacent a subsea hydrocarbon production tree and associated equipment. One or more resonant inductive circuits are provided to assure a reliable, strong output signal. This resonance is obtained by using the transformer action of the inductive core member to reflect a capacitive value to the primary coil whereby capacitive elements may be selected which are more compatible with the subsea environment than could otherwise be obtained. Variations in the resonant frequency of the inductive elements are accommodated by providing a FM signal sweeping through a frequency range selected to accommodate the anticipated variations. Resonant circuits maximize signal transfer across the sensor and provide an amplitude modulated FM signal for demodulation. The peak amplitude of the amplitude modulated signal is functionally related to the absence or presence of hydrocarbons and is detected. The peak amplitude may be monitored directly or may be compared with a preselected threshold voltage for triggering a response to the presence of hydrocarbons.

Figure 3:
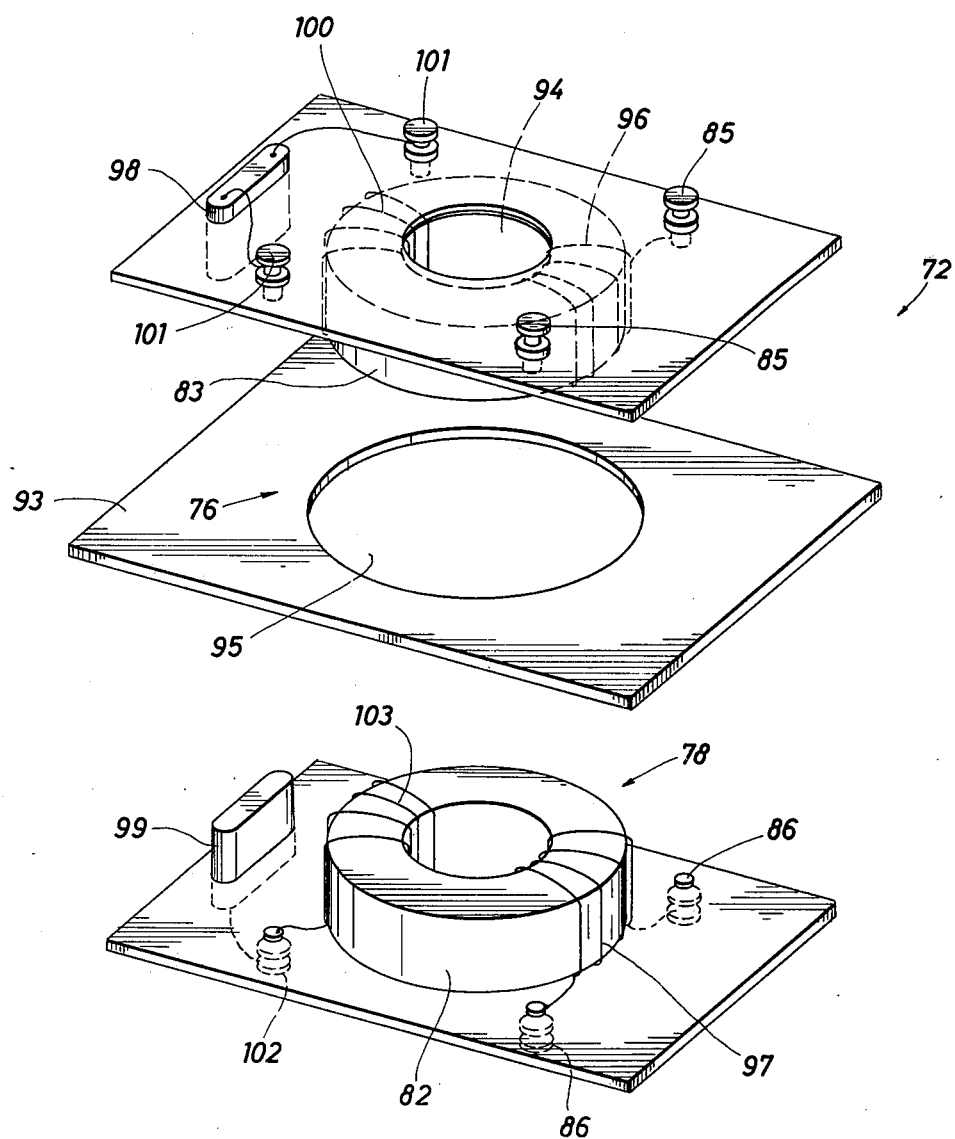
FIG. 3 is a pictorial illustration of an exploded sensor assembly.

Referring now to FIG. 3, there is shown a pictorial illustration of an exploded sensor coil assembly 72 suitable for implementing the present invention. Induction coil assembly 72 preferably comprises two inductive coils 76 and 78 placed in a parallel spaced-apart relationship, as hereinabove described. Induction coils 76 and 78 may conveniently be toroidal, having toroidal core elements 83 and 82, respectively, and correspond to the inductive elements 36 and 46 shown in FIG. 2 and heretofore described. Primary winding posts 85 and 86 are mounted adjacent induction coils 76 and 78, respectively.

One of the induction coils 76, 78 serves as a transmitting inductive element and the other serves as a receiving inductive element, as hereinabove described. The arrangement is conveniently interchangeable. Primary coils 96 and 97 are provided in inductive element 76 and 78, respectively, and are internally connected with signal leads 85 and 86, respectively. Each inductive element forms a closed toroidal element creating a magnetic field within its toroidal core and thereby acting to produce an electrical current in conductive substances (e.g., seawater) within the central aperture 94 and forming at least one closed current path (see FIG. 2, item 44) common to both elements. An electrical current generated in the closed circuit path by either induction coil 76 or 78 will be detected by the other induction coil to a degree dependent on conductivity of the current path linking the two toroidal cores.

Capacitive elements 98 and 99 are connected with auxiliary winding posts 101 and 102, respectively, and thence to auxiliary windings 100 and 103, respectively, placed about core elements 83 and 82, respectively. Auxiliary windings 100 and 103 act to reflect a capacitance into the primary windings 96 and 97, respectively, to produce a resonant circuit, as described for FIG. 2.

In final asssembly, inductive elements 76 and 78 are placed in a parallel relationship, separated by electrostatic shield 93 having a central aperture 95. Thus, the entire sensor coil assembly 72 forms a closely packed assembly having inductive elements 76 and 78 in close proximity with a central aperture 94 extending through the entire assembly 72.

A typical value of inductance for the inductive element where $N_1=10$ turns and $N_2=50$ turns is about 35 mh. If a convenient capacitance value of 0.01 $\mu f$ is then selected, the resulting resonant frequency is approximately 85 KHz, well within the sweeping frequency range of 75-100 KHz hereinabove described. As hereinabove discussed, a low relative permeability cores 82 and 83 may be provided having a low relative permeability, e.g., $\mu=125$, with a related low rate of change as a function of temperature.

Figure 4:
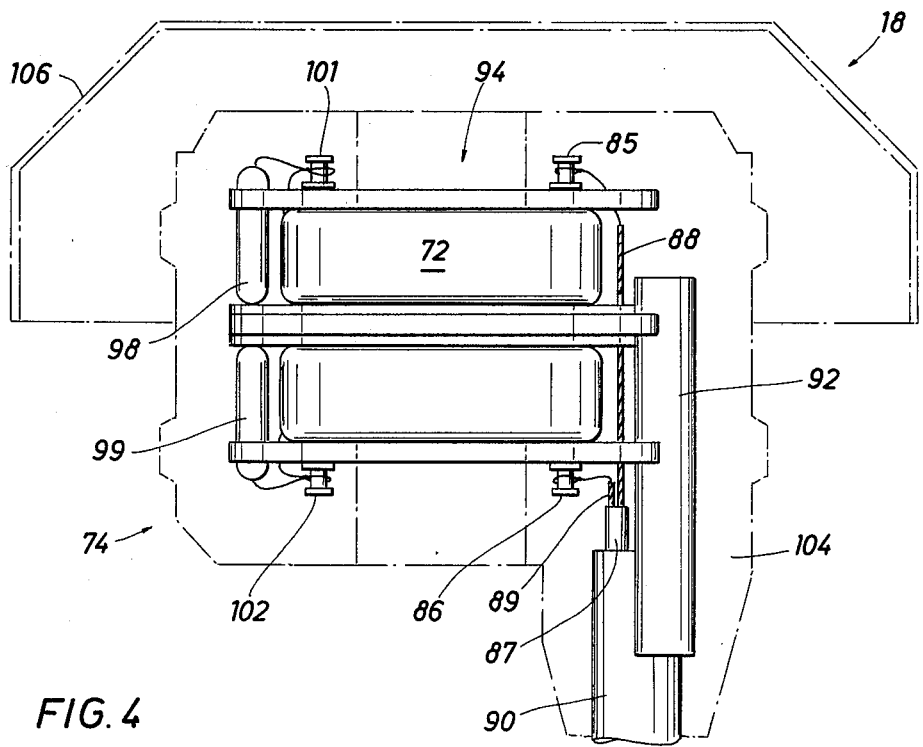
FIG. 4 is a pictorial illustration, in partial cutaway, of an assembled detector unit.

A completely assembled sensor assembly 18 is shown in FIG. 4. Induction coil assembly 72 is connected to cable assembly 87 by connecting signal transmitting leads 88 and 89 to primary winding posts 85 and 86, respectively. Signal transmitting leads 88 and 89 are packaged with a dielectric sleeve 87 and a protective cable sheath 90 which is suitable for use in a subsea environment.

The assembled induction coils 76 and 78 and cable sheath 90 are interconnected to support post 92 to form a completed assembly. If this entire assembly is to be immersed in a subsea environment, it is preferably encapsulated to provide resistance to the destructive effects of the environment. In one embodiment, the assembled elements are placed in a mold assembly with a removable shaft element filling central aperture 94 and the entire assembly coated with a suitable material 104, such as vulcanized neoprene. A final coating may be applied with the molding shaft removed from the annular mold in order to provide a protective covering for the surface area of central aperture 94. Thus, a completely sealed sensor assembly 74 is provided having central aperture 94 therethrough for communicating surrounding environmental medium through central aperture 94.

When mounted as a hydrocarbon detector 18, as shown in FIG. 1, sensor assembly 74 is inserted into an inverted "bucket" 106 assembly. Inverted bucket 106 may be formed in any convenient configuration acting to provide a shape suitable for collecting evolving hydrocarbons escaping from equipment at the selected location. As the hydrocarbons escape, the normal environmental medium, such as sea water, is displaced from within inverted bucket 106 until the conductance of the path through aperture 94 is significantly reduced, thereby reducing the signal received by the receiving inductive element. Although not depicted, a controllable valve assembly may be placed in a elevated region of inverted bucket 106 for venting the evolved hydrocarbons therein and reset sensor assembly 18. This technique would be desirable for monitoring the rate of leakage from an area or resetting the sensor system 18, once the leak is corrected.

Figure 5:
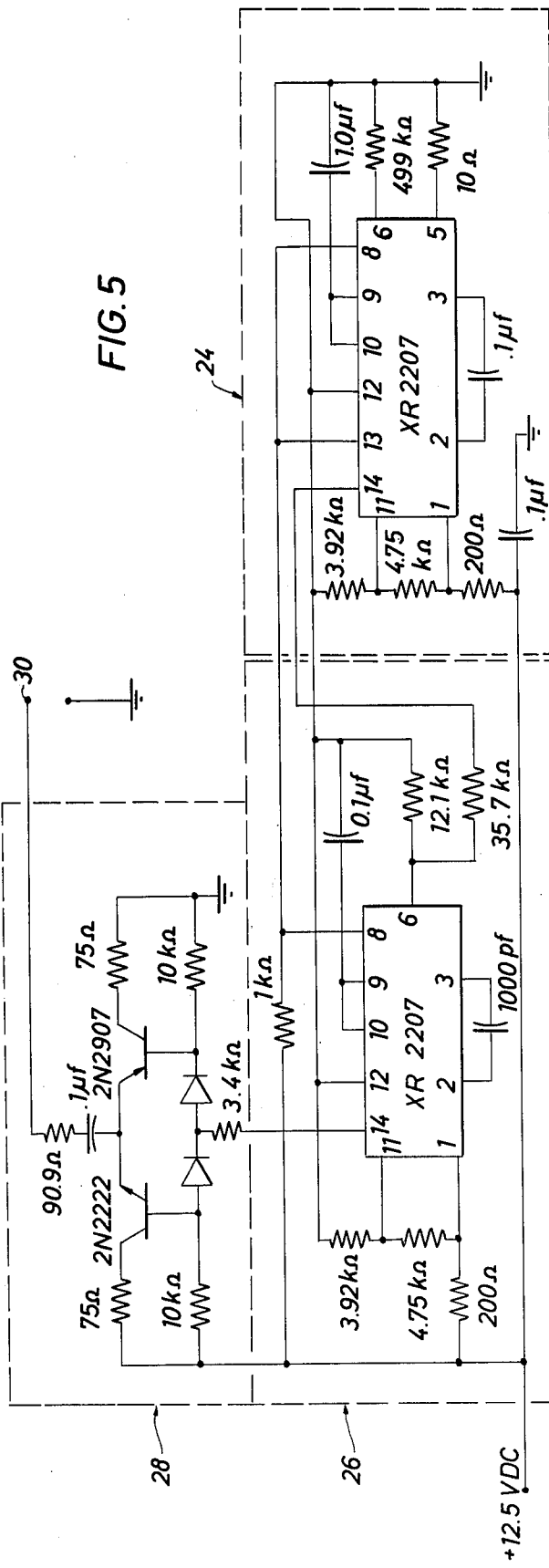
FIG. 5 is a schematic diagram of a signal generating circuit used in the apparatus of FIG. 2.

Referring now to FIG. 5, there is particularly depicted a preferred embodiment of a circuit for generating frequency sweeping signal 30 which activates the transmitting inductive element. Sweep voltage generator 24 is composed of a function generator (XR 2207) in a conventional circuit design to produce a linear ramp voltage output which is presented to a voltage controlled oscillator circuit 26. As shown in FIG. 5, the circuit is connected to obtain capacitor charging from a constant current source to produce a linear voltage ramp output.

Circuit 26 is also formed from an integrated circuit element (XR 2207) generating selected functions to produce an output signal having a periodically varying frequency covering the frequency range of interest. In a preferred embodiment, generator 24 is running at a low frequency compared to oscillator 26. The voltage ramp output from generator 24 is applied to a control capacitor within oscillator 26 to set the oscillator 26 frequency. A preferred ramp frequency output from circuit 24 is 40 Hz, which is selected to be low enough to obtain a peak sensor output at the resonant frequency and high enough to maintain an output at a peak detector hereinafter discussed. The sweeping frequency output from circuit 26 preferably covers a range of 75-100 KHz.

The output from the voltage controlled oscillator is presented to amplifier circuit 28 formed from transistor elements arranged in conventional amplifier configuration. The amplified sweeping frequency output signal from circuit 28 forms the exciting signal 30 which is transmitted to the transmitting inductive element as hereinabove discussed.

Figure 6:
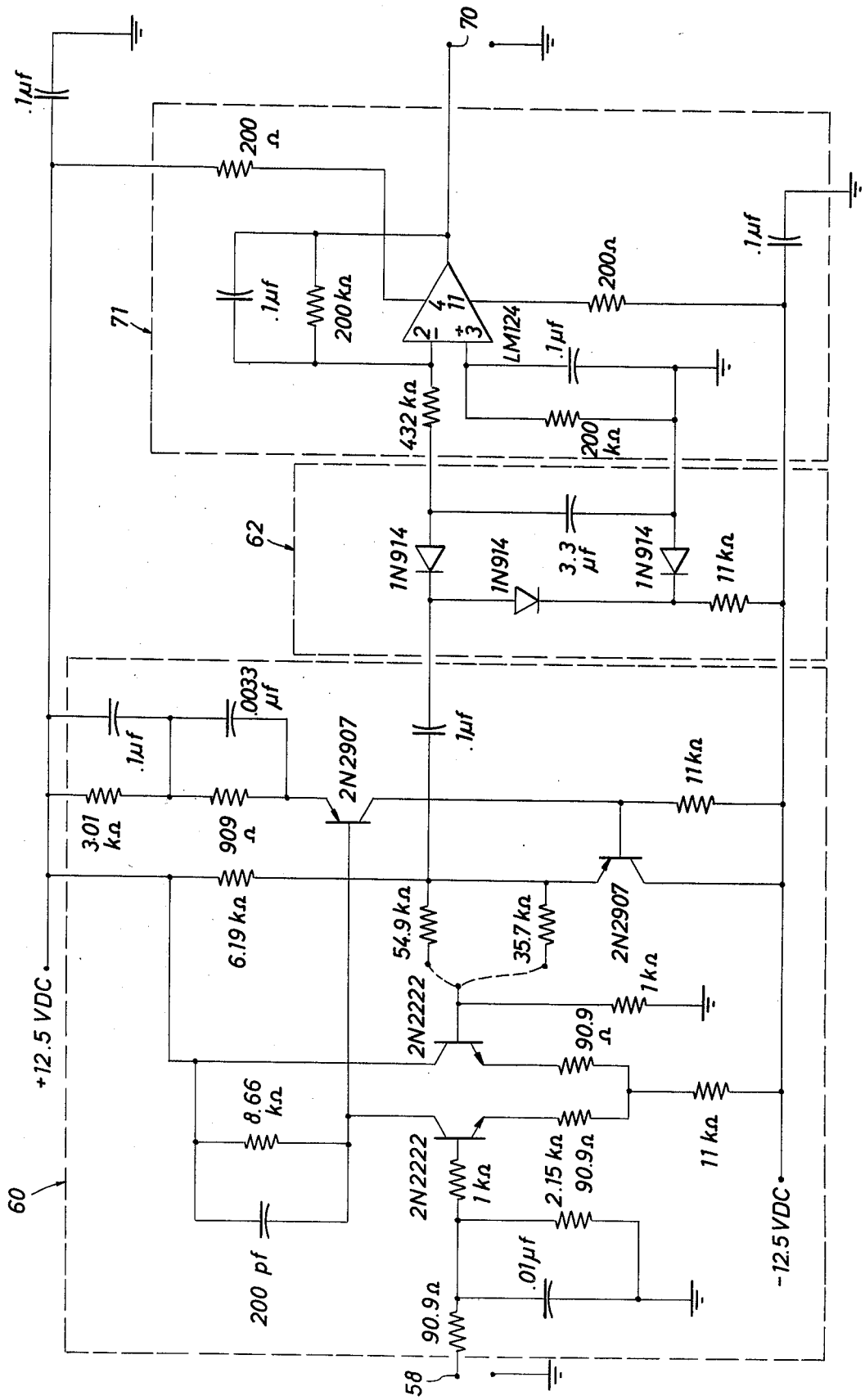
FIG. 6 is a schematic diagram of signal detecting circuits used in the apparatus of FIG. 2.

Referring now to FIG. 6, there is shown a preferred embodiment of circuitry for processing output signal 58 (FIG. 2) from the sensor assembly. Amplifier 60 is provided for receiving input signal 58. Transistor elements are conventionally arranged in a staged configuration to produce an amplified output signal to peak detecting circuit 62. The amplifier stage may be equipped with a gain control so that a reduced gain may be used where reduced signal attenuation is obtained (e.g., where magnetic cable couplers are not required). For example, amplifier 60, as shown in FIG. 5, provides for strapping either a 35.7 K ohm or 54.9 K ohm resistor in the circuit to accommodate either direct or inductive coupling, respectively, in the cable connections. Conventional bandpass filtering may also be provided to eliminate spurious or noise signals.

The processed and amplified incoming signal is then presented to peak detector 62 conventionally designed to produce a d-c voltage having a magnitude functionally related to the peak-to-peak amplitude of the incoming signal 58. By appropriate selection of the components, the peak value of the incoming signal may be held and presented to circuit 71. More particularly, the output voltage appears across the 3.3 µf capacitor within peak detector 62. The capacitance value is selected to cooperate with the periodicity of the sweeping signal whereby and the discharge time is long relative to the periodicity. Circuit 71 may be a d-c amplifier as depicted in FIG. 6. In one embodiment, a low pass frequency filter arrangement may be provided where only the amplitude characteristics are amplified and not any residual carrier. The output signal in analog form may be transmitted to alarm or monitoring equipment located on the surface.

Alternately, the peak value signal from peak detector 62 may also be presented to comparator circuit 68 (FIG. 2) which compares the peak detected signal, which is functionally related to the conductivity of the environmental medium about the sensors, with a selected reference signal. The reference signal may be conveniently selected to correspond to a low peak signal such as would exist when the sea water adjacent assembly 74 has been replaced with low conductivity material, such as hydrocarbon products escaping from the subsea production equipment. Thus, when the peak-to-peak amplitude of the received FM signal decreases to the reference level, an output indication 70 (FIG. 2), which may be a shift in logical output states, is obtained indicating the presence of hydrocarbons about the sensor elements. In a fail safe embodiment, a continuous logical output is obtained from comparator circuit 68 (FIG. 2) until hydrocarbons are detected, whereupon the output logic would change and be detected when the control system interrogates the detector system output. This condition would also be obtained upon failure of the system components so that various interconnected control systems and system operators would be alerted.

Many other alternative forms of the present invention will, of course, be apparent from the foregoing methods and apparatus. Accordingly, the structures and techniques hereinabove depicted and discussed are illustrative only, and are not intended as limitations on the scope of the present invention.

What is claimed is:

1. In a subsea hydrocarbon production installation which includes at least first and second production tree assemblies spaced apart on the sea floor, at least one electro-hydraulic control module located at the sea floor at a substantial distance from at least said first tree assembly, and a plurality of elongated cables extending from said module to at least said first tree assembly for conducting tree-assembly condition indicative signals from said first tree assembly to said control module and other signals from said module to said first tree assembly and in which said cables are coupled to said control module by means of magnetic coupling devices which permit physical removal of said module from the sea floor without exposing current carrying conductors to the sea-water environment, a hydrocarbon-leak detecting and reporting subsystem comprising:

means contained within said control module for providing a frequency-modulated interrogation signal with the frequency of said signal varying as a function of time over a preselected frequency range;

means comprising at least one of said cables and at least one of said magnetic coupling devices for conducting said signal to said first tree assembly;

hydrocarbon-presence-responsive sensor means, located adjacent a portion of the hydrocarbon-containing equipment of said first tree assembly, for transmitting and attenuating said signal as a predetermined function of the amount of hydrocarbon compounds in an environmental medium adjacent said sensor means;

means comprising at least one of said cables and one of said magnetic coupling devices for conducting said attenuated signal to the interior of said control module;

a peak detector in said module responsive to said attenuated signal for producing a hydrocarbon-presence-indicative electrical signal whose amplitude is substantially independent of resonant frequency variations of said sensor means; and means responsive to the signal produced by said peak detector for communicating hydrocarbon-presence-indicative intelligence signals to a sea-surface or land-based facility.

2. Apparatus according to claim 1, wherein said sensor means has a resonant frequency within said preselected frequency range.

3. Apparatus according to claim 1 or claim 2, wherein said sensor means further comprises:

a pair of inductive elements each having a core element with a central aperture therethrough and a primary winding thereon, said inductive elements having said central apertures substantially aligned to admit said environmental medium, said environmental medium surrounding and electrically interconnecting said pair of inductive elements to attenuate said interrogation signal.

4. Apparatus according to claim 3, wherein at least one of said inductive elements further comprises a capacitive element for resonating said inductive element within said preselected frequency range.

5. Apparatus according to claim 4, wherein said capacitive element further includes:

a capacitor having a relatively low value of capacitance, an auxiliary winding about said core element and connected to said capacitor, said auxiliary winding and said primary winding having a turns ratio producing a relatively large effective capacitance to resonate said inductive element.

6. A hydrocarbon sensor system, comprising:

a transmitting inductive element responsive to an excitation signal for generating an electrical current in an environmental medium adjacent said element;

a receiving inductive element responsive to said electrical current in said medium for providing an output signal;

at least one of said inductive elements having a capacitive element coupled thereto for resonating said one inductive element at a frequency within a predetermined frequency range;

said excitation signal being frequency modulated over a frequency range substantially corresponding to said predetermined range, and means for monitoring said output signal to indicate the presence of hydrocarbons in the vicinity of said inductive elements.

7. Apparatus according to claim 6, where said transmitting and receiving inductive elements each comprise:
   a core element having predetermined magnetic response characteristics and encircling a portion of said environmental medium; and
   a primary signal winding arranged about said core element for producing or detecting said electrical current in said environmental medium.

8. Apparatus according to claim 7, wherein said capacitive element further includes:
   a capacitor having a selected capacitance;
   an auxiliary winding on said core element connected to said capacitor,
   said auxiliary winding and said primary winding having a turns ratio cooperating with said capacitance to reflect a value of said capacitance effective to resonate said inductive element at a resonant frequency within said selected frequency range.

9. Apparatus according to claims 7 or 8, wherein said magnetic response characteristics include a relatively low magnetic permeability.

10. Apparatus according to claims 6, 7, or 8, wherein said means for monitoring said output signal comprises:
    detection means for detecting said output signal as said excitation signal corresponds to said resonant frequency.

11. Apparatus according to claim 10, further including:
    peak signal detector means for deriving an amplitude analog signal functionally related to a peak output from said detection means during each sweep of said frequency sweeping signal.

12. In a hydrocarbon sensor system using inductive elements coupled by a conductive environmental medium and sensing the conductance of the surrounding medium, a tuned inductive element, comprising:
    a core having selected magnetic characteristics;
    a primary coil wound about said core a first number of turns;
    a secondary coil wound about said core a second number of turns; and
    a capacitor having a relatively small capacitance connected across said secondary coil;
    the ratio of said first number of turns to said second number of turns being effective to reflect a relatively large capacitance from said capacitor to resonate with said primary coil within a predetermined frequency range.

13. The subcombination according to claim 12, wherein said selected magnetic characteristics include a relatively low magnetic permeability.

14. A method for detecting the presence of hydrocarbons in a conductive medium where escaping hydrocarbons are trapped to displace the conductive medium comprising the steps of:
    forming a pair of inductive elements so that said pair are collectively tuned to resonance at a frequency within a selected frequency range;
    generating a signal which is frequency modulated across at least said selected frequency range;
    applying said signal to a first inductive element of said pair to produce an electrical current circulating in the conductive medium adjacent said first element; and
    producing a hydrocarbon-presence-indicative signal by detecting the peak-to-peak amplitude of a frequency modulated voltage signal induced in the second inductive element of said pair by said circulating electrical current in the conductive medium.

15. A method according to claim 14, including:
    forming at least one inductive element of said pair to include a primary winding, an auxiliary winding and a resonating capacitance coupled to said auxiliary winding.

16. A method according to claim 15, wherein said auxiliary winding has a larger number of turns than the primary winding so that the capacitance reflected to the primary winding exceeds the actual value of the capacitance at said auxiliary winding.

17. A method according to claims 14, 15 or 16, further comprising:
    forming and relatively positioning said inductive elements so that the amplitude of the voltages induced in the second inductive element of said pair is indicative of the magnitude of the electrical current induced in the conductive medium adjacent said first inductive element.

* * * * *